United States Patent [19]

Seele et al.

[11] Patent Number: 5,231,110
[45] Date of Patent: Jul. 27, 1993

[54] FUNGICIDAL COMPOSITION

[75] Inventors: Rainer Seele, Fussgoenheim; Reinhold Saur, Boehl-Iggelheim; Klaus Schelberger, Goennheim; John-Bryan Speakman, Bobenheim, all of Fed. Rep. of Germany

[73] Assignee: BASF Aktiengesellschaft, Ludwigshafen, Fed. Rep. of Germany

[21] Appl. No.: 903,758

[22] Filed: Jun. 25, 1992

[30] Foreign Application Priority Data

Jul. 6, 1991 [DE] Fed. Rep. of Germany ....... 4122474

[51] Int. Cl.$^5$ .................. A01N 43/50; A01N 43/64
[52] U.S. Cl. ..................... 514/383; 514/399
[58] Field of Search ................. 514/383, 399

[56] References Cited

U.S. PATENT DOCUMENTS

| | | | |
|---|---|---|---|
| 4,652,580 | 3/1987 | Janssen et al. | 514/383 |
| 4,753,954 | 6/1988 | Janicke et al. | 514/317 |
| 4,906,652 | 3/1990 | Karbach et al. | 514/383 |
| 5,106,848 | 4/1992 | Seele et al. | |

FOREIGN PATENT DOCUMENTS

| | | |
|---|---|---|
| 0040007 | 11/1981 | European Pat. Off. |
| 0072156 | 2/1983 | European Pat. Off. |
| 0196038 | 10/1986 | European Pat. Off. |

OTHER PUBLICATIONS

Brighton Crop Protection Conference, Pests and Diseases, 1990, pp. 837–845, A. Akers, et al., "Uptake Transport and Mode of Action of BAS 480 F, A New Triazole Fungicide".
British Crop Protection Conference–Pests and Diseases, 1986, pp. 539–546, S. J. Kendall, "Cross-Resistance of Triadimenol-Resistance Fungal Isolates to Other Sterol C–14 Demethylation Inhibitor Fungicides".

Primary Examiner—Allen J. Robinson
Attorney, Agent, or Firm—Oblon, Spivak, McClelland, Maier & Neustadt

[57] ABSTRACT

A fungicidal composition of 2-(1,2,4-triazol-1-ylmethyl)-2-(4-fluorophenyl)-3-(2-chlorophenyl)-oxirane of the formula

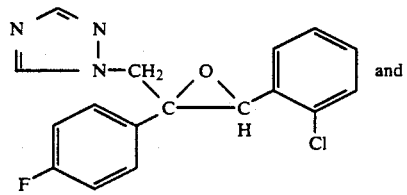

and 1-[N-n-propyl-N-2-(2,4,6-trichlorophenoxy)-ethylcarbamoyl]-imidazole

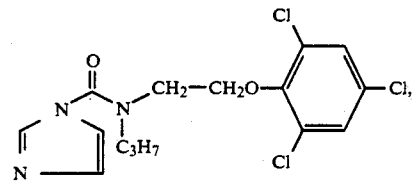

and methods of combating fungi with this composition.

6 Claims, No Drawings

FUNGICIDAL COMPOSITION

The present invention relates to fungicidal compositions having a synergistic fungicidal action and methods of combating fungi with these compositions.

The use of 2-(1,2,4-triazol-1-ylmethyl)-2-(4-fluorophenyl)-3-(2-chlorophenyl)-oxirane of the formula

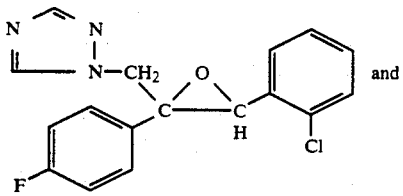

I or one of its salts as fungicide has been disclosed (EP 196,038). The use of the active ingredient 1-[N-n-propyl-N-2-(2,4,6-trichlorophenoxy)-ethylcarbamoyl]-imidazole of the formula

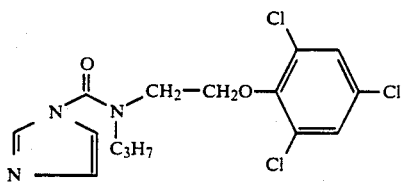

II or its metal complex compounds as fungicide has also been disclosed (EP 40 007).

We have now found that a composition of
a) 2-(1,2,4-triazol-1-ylmethyl)-2-(4-fluorophenyl)-3-(2-chlorophenyl-oxirane of the formula

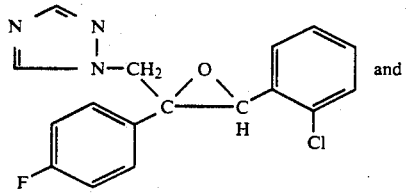

I b) 1-[N-n-propyl-N-2-(2,4,6-trichlorophenoxy)-ethylcarbamoyl]-imidazole of the formula

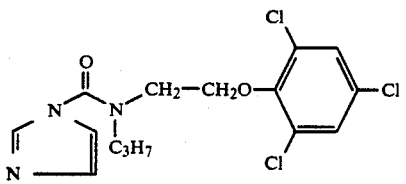

II has a synergistic fungicidal action. The mixture ratio (by weight) of compounds a) and b) is such that a synergistic fungicidal action occurs, for example a ratio of a):b) of from 5:1 to 1:5, especially form 3:1 to 1:3, and preferably form 2:1 to 1:2. The synergistic effect of the composition is apparent from the fact that the fungicidal action of the composition of a)+b) is greater than the sum of the fungicidal actions of a) and b).

2-(1,2,4-triazol-1-ylmethyl)-2-(4-fluorophenyl)-3-(2-chlorophenyl-oxirane (component a) may be present in four stereoisomeric forms, whose fungicidal actions differ. Preferred are the two cis isomers, i.e., those enantiomers in which the triazolylmethyl group and the 2-chlorophenyl group are on the same side of the oxirane ring.

The invention encompasses mixtures of pure isomers of compound a and b, especially mixtures of one cis enantiomer of 2-(1,2,4-triazol-1-ylmethyl)-2-(4-fluorophenyl)-3-(2-chlorophenyl)-oxirane with 1-[N-n-propyl-N-2-(2,4,6-trichlorophenoxy)-ethylcarbamoyl]-imidazole.

The invention also encompasses agents in which active ingredient component a (2-(1,2,4-triazol-1-ylmethyl)-2-(4-fluorophenyl)-3-(2-chlorophenyl)-oxirane) is present predominantly in the form of the two cis enantiomers.

The active ingredients of the formulae a and b may also be present in the form of their slats or metal complexes. These mixtures are also encompassed by the invention.

Salts are produced by reaction with acids, e.g., hydrohalic acids such as hydrofluoric acid, hydrochloric acid, hydrobromic acid or hydroiodic acid, or sulfuric acid, phosphoric acid, nitric acid or organic acids such as acetic acid, trifluoroacetic acid, trichloroacetic acid, propionic acid, glycolic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid and 1,2-naphthalenedisulfonic acid.

Metal complexes may contain either only one component a or one component b, or several components b. Metal complexes may also be produced which contain both components a and b in a mixed complex.

Metal complexers are prepared form the basic organic molecule and an inorganic or organic metal salt, for example the halides, nitrates, sulfates, phosphates, acetates, trifluoroacetates, trichloroacetates, propionates, tartrates, sulfonates, salicylates and benzoates of metals of the second main group, such as calcium and magnesium, and of the third and fourth main groups, such as aluminum, tin or lead, and of the first to eight sub-group, such as chromium, manganese, iron, cobalt, nickel, copper and zinc. Elements of the fourth sub-group, especially copper, are preferred. It is possible for the metals to have a variable valence. The metal complexes may be mononuclear or polynuclear, i.e., they may contain one or several organic molecule moieties as ligands, for example mixed complexes of 2-(1,2,4-triazol-1-ylmethyl)-2-(4-fluorophenyl)-3-(2-chlorophenyl)-oxirane and 1-[N-n-propyl-N-2-(2,4,6-trichlorophenoxy)-ethylcarbamoyl]-imidazole.

Usually, the pure active ingredients a) and b) are advantageously used, to which other active ingredients such as insecticides, acaricides, nematicides, herbicides, other fungicides, growth regulators and/or fertilizers may be added.

The fungicidal compositions according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the composition according to the invention as possible.

Normally, the plants are sprayed or dusted with the compositions, or the seeds of the plants are treated with the compositions.

The formulations are prepared in known manner, e.g., by extending the composition with solvents and/or carriers, if desired using emulsifiers and dispersants; if water is employed as diluent, other organic solvents may also be used as auxiliary solvents. Examples of suitable auxiliaries are essentially solvents such as aromatics (e.g., xylene), chlorinated aromatics (e.g., chlorobenzenes), paraffins (e.g., petroleum fractions), alcohols (e.g., methanol, butanol), ketones (e.g., cyclohexanone), amines (e.g., ethanolamine, dimethylformamide), and water; carriers such as natural rock flours (e.g., kaolins, clays, talc and chalk), and synthetic rock flours (e.g., highly disperse silicic acid, silicates); emulsifiers such as nonionic and anionic emulsifiers (e.g., polyoxyethylene fatty alcohol ethers, alkyl sulfonates and aryl sulfonates), and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The compositions are extremely effective on a broad spectrum of phytopathogenic fungi, in particular those form the class consisting of the Ascomycetes and Basidiomycetes. Some of them have a systemic action and can be used as foliar and soil fungicides.

The compositions are of particular interest for controlling large number of fungi in various crops or their seeds, especially wheat, rye, barley, oats, rice Indian corn, lawns, cotton, soybeans, coffee, sugar cane, grapes and other fruit, and ornamentals, and in vegetables such as cucumbers, beans and cucurbits, and the seeds of these plants.

The compositions are applied by treating the fungi, or the seed, plants or materials to be protected against fungus attack, or the soil with a fungicidally effective amount of them.

The composition may be applied before or after infection of the materials, plants or seed by the fungi.

The compositions are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
*Ustilago* species in cereals and sugar cane,
*Venturia inaequalis* (scab) in apples,
*Helminthosporium* species in cereals,
*Septoria nodorum* in wheat,
*Botrytis cinerea* (gray mold) in strawberries and grapes,
*Cercospora arachidicola* in ground nuts,
*Pseudocercosporella herpotrichoides* in wheat and barley,
*Pyricularia oryzae* in rice,
*Phytophthora infestans* in potatoes and tomatoes,
*Fusarium* and *verticillium* species in various plants,
*Plasmopara viticola* in grapes,
*Alternaria* species in fruit and vegetables.

The novel compositions may also be sued for protecting materials (timber), e.g., against *Paecilomyces variotii*.

The fungicidal agents generally contain from 0.1 to 95, and preferably from 0.5 to 90, wt. % of active ingredient.

The application rates of the compositions according to the invention depend on the effect desired, and range form 0.02 to 3 kg of active ingredient composition per hectare.

When the compositions are used for treating seed, application rates of from 0.001 to 50, and preferably from 0.01 to 10, g per kg of seed are generally required.

Experiments 1 and 2

Eradicative fungicidal action on eyespot disease in wheat

Wheat plants of the "Rektor" variety were inoculated at the 3-leaf stage with *Pseudocercosporella herpotrichoides*, the eyespot pathogen, and treated 10 days after inoculation (symptoms of attack just perceptible at the leaf sheaths or the coleoptiles) with aqueous formulations of the active ingredients in the concentrations stated. The amount of water was 400 liters/ha.

The plants were cultivated in the greenhouse for 30 days at 5° to 10° C. The experiment was then evaluated by assessing the area attacked and the intensity of attack at the base of the stalks on a 0 to 100 scale (0 denoting no attack, and 100 denoting a completely rotten stalk base). These figures were converted into action percentages: 0 (no attack) is 100% action, and 100 rotten stalk base) is 0% action. The actions the active ingredient combinations would be expected to have were calculated according to the Colby formula*) and compared with the actions observed. The are shown as the results of Experiments 1 and 2.

The values for the fungicidal action vary between the various experiments because the plants in the experiments suffered form varying degrees of attack, so the figures for the fungicidal attack also vary. For this reason only the results in the same experiment can be compared.

Colby, S. R. "Calculating synergistic and antagonistic responses of herbicide combinations", Weeds, 15, pp. 20-22, 1967

Colby formula $E = X + Y - \frac{XY}{100}$

E = expected degree of action, expressed in % of the untreated control, when active ingredients A nd B are sued in concentrations of m and n%

X = degree of action, expressed in % of the untreated control, when active ingredient A is used in a concentration of m%

Y = degree of action, expressed in % of the untreated control, when active ingredient B is used in a concentration of n%

Experiment 1
Pseudocercosporella herpotrichoides test (eradicative) in wheat

| Active ingredient | Active ingredient concentration in spray liquor in % | Action in % of untreated control |
| --- | --- | --- |
| Control (untreated) | — | 0 |
| I | 0.05 | 28 |
| II | 0.05 | 35 |
| Compositions according to the invention | | |
| I + II (ratio 1:3) | 0.01 + 0.03 | 68 |
| I + II (ratio 3:1) | 0.03 + 0.01 | 64 |

These results show that 0.04% (0.01+0.03 and 0.03+0.01) of the composition has a better fungicidal action than 0.05% of the individual active ingredients.

In parallel experiments, strains of *Pseudocercosporella herpotrichoides* were tested as pathogens which were resistant and non-resistant to the prior art fungicidal active ingredient carbendazim. The fungicidal compositions had an equally good action on both groups of pathogens.

Experiment 2
Pseudocercosporella herpotrichoides test (eradicative) in wheat

| Active ingredient | Active ingredient concentration in spray liquor in % | Action in % of untreated control |
| --- | --- | --- |
| Control (untreated) | — | 0 |
| I | 0.1 | 62 |
| | 0.05 | 25 |
| II | 0.1 | 65 |
| | 0.05 | 33 |
| Compositions according to the invention | Observed action | Calculated action*) |
| I + II 0.05 + 0.05 ratio 1:1 | 85 | 49.7 |
| I + II 0.1 + 0.1 ratio 1:1 | 100 | 86.7 |
| I + II 0.1 + 0.05 ratio 2:1 | 100 | 74.5 |
| I + II 0.05 + 0.1 ratio 1:2 | 100 | 73.7 |

*) Calculated according to the Colby formula

It is apparent from the results of these experiments that the observed action at all ratios is greater than the action calculated in advance by the Colby formula.

In parallel experiments, strains of Pseudocercosporella herpotrichoides were tested as pathogens which were resistant and non-resistant to the prior art fungicidal active ingredient carbendazim. The fungicidal compositions had an equally good action on both groups of pathogens.

We claim:
1. A fungicidal composition comprising a synergistically fungicidally effective amount of a composition of
a) 2-(1,2,4-triazol-1-ylmethyl)-2-(4-fluorophenyl)-3-(2-chlorophenyl)-oxirane of the formula

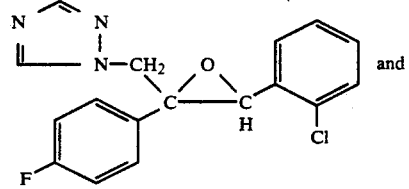

and b) 1-[N-n-propyl-N-2-(2,4,6,-trichlorophenoxy)ethylcarbamoyl]-imidazole of the formula

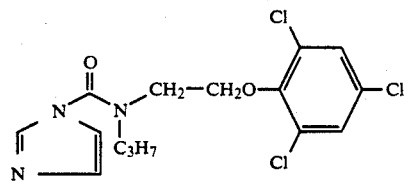

in a ratio of a:b of from 5:1 to 1:5.

2. A fungicidal composition according to claim 1, wherein the ratio of a:b is from 3:1 to 1:3.

3. A fungicidal composition according to claim 1, wherein the ratio of a:b is from 2:1 to 1:2.

4. A process for combating fungi, comprising the step of applying a synergistically fungicidally effective amount of a composition of comprising
a) 2-(1,2,4-triazol-1-ylmethyl)-2-(4-fluorophenyl)-3-(2-chlorophenyl)-oxirane of the formula

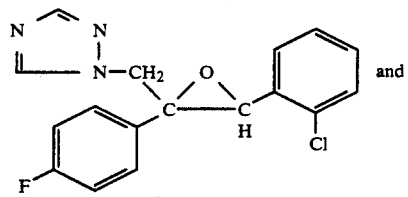

and b) 1-[N-n-propyl-N-2-(2,4,6-trichlorophenoxy)ethylcarbamoyl]-imidazole of the formula

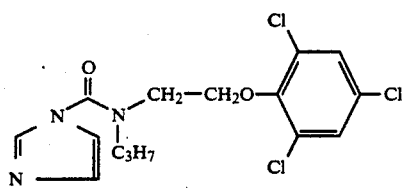

in a ratio of a:b from 5:1 to 1:5 to the fungi, or to the materials, areas, plants or seed threatened by fungus attack.

5. A process for combating fungi according to claim 4, wherein the ratio of a:b is from 3:1 to 1:3.

6. A process for combating fungi according to claim 4, wherein the ratio of a:b is from 2:1 to 1:2.

* * * * *